United States Patent
Reddy et al.

(10) Patent No.: US 9,540,406 B2
(45) Date of Patent: Jan. 10, 2017

(54) PROCESS FOR FOSAPREPITANT

(75) Inventors: Bandi Parthasaradhi Reddy, Hyderabad (IN); Kura Rathnakar Reddy, Hyderabad (IN); Dasari Muralidhara Reddy, Hyderabad (IN); Thungathurthy Srinivasa Rao, Hyderabad (IN); Bandi Vamsi Krishna, Hyderabad (IN)

(73) Assignee: HETERO RESEARCH FOUNDATION, Andhra Pradesh (IN)

( * ) Notice: Subject to any disclaimer, the term of this patent is extended or adjusted under 35 U.S.C. 154(b) by 155 days.

(21) Appl. No.: 14/123,290

(22) PCT Filed: May 21, 2012

(86) PCT No.: PCT/IN2012/000360
§ 371 (c)(1),
(2), (4) Date: Dec. 2, 2013

(87) PCT Pub. No.: WO2012/164576
PCT Pub. Date: Dec. 6, 2012

(65) Prior Publication Data
US 2014/0107337 A1     Apr. 17, 2014

(30) Foreign Application Priority Data

Jun. 3, 2011   (IN) .......................... 1927/CHE/2011

(51) Int. Cl.
*C07F 9/6558*        (2006.01)

(52) U.S. Cl.
CPC ................................. *C07F 9/65583* (2013.01)

(58) Field of Classification Search
CPC .................................................... C07F 9/65583
See application file for complete search history.

(56) References Cited

U.S. PATENT DOCUMENTS

2011/0130366 A1   6/2011  Bhatt et al.

FOREIGN PATENT DOCUMENTS

| WO | 2010018595 A2 | 2/2010 |
| WO | 2010034032 A2 | 3/2010 |
| WO | 2011045817 A2 | 4/2011 |

OTHER PUBLICATIONS

International Search Report and Written Opinion; International Application No. PCT/IN2012/000360; International Filing Date May 21, 2012; 8 pages.
New SiliaBond Metal Scavenger Silia Bond DMT (Dimercaptotriazine) Flyer, Silicycle Ultrapure Silica Gels, www.SiliCycle.com, 2008, 2 pages.
SiliaBond Metal Scavengers, Silicycle UltraPure Silica Gels, www.SiliCycle.com, 2008, 20 pages.
Silicycle UltraPure Silica Gels, Purification and Synthesis, Silica gels, Catridges, SPE, TLC, Scavengers and Reagents, 2008 Catalog; SiliCycle.com; 129 pages.

*Primary Examiner* — Matthew Coughlin
(74) *Attorney, Agent, or Firm* — Cantor Colburn LLP

(57) ABSTRACT

The present invention provides a novel process for reducing palladium content in fosaprepitant dimeglumine.

14 Claims, No Drawings

PROCESS FOR FOSAPREPITANT

CROSS-REFERENCE TO RELATED APPLICATIONS

This application is a U.S. national stage of international application No. PCT/IN2012/000360, filed on May 21, 2012, the disclosure of which is incorporated herein by reference in its entirety. Priority is claimed from IN Patent Application No. 1927/CHE/2011, filed on Jun. 3, 2011, the disclosure of which is also incorporated herein by reference in its entirety.

FIELD OF THE INVENTION

The present invention provides a novel process for reducing palladium content in fosaprepitant dimeglumine.

BACKGROUND OF THE INVENTION

Fosaprepitant, chemically [3-{[(2R,3S)-2-[(1R)-1-[3,5-bis(trifluoromethyl)phenyl]ethoxy]-3-(4-fluorophenyl)morpholin-4-yl]methyl}-5-oxo-2H-1,2,4-triazol-1-yl]phosphonic acid and has the structural formula:

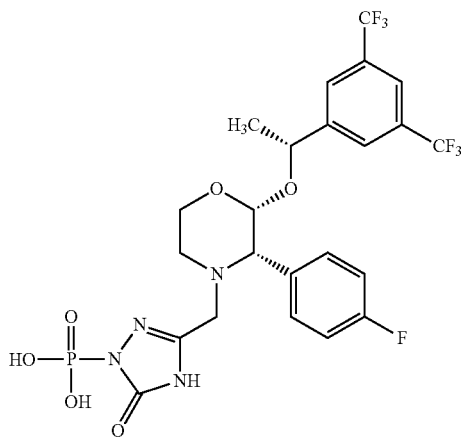 [SMILES: C[C@@H](O[C@H]1OCCN(Cc2nn(P(=O)(O)O)c(=O)[nH]2)[C@H]1c1ccc(F)cc1)c1cc(C(F)(F)F)cc(C(F)(F)F)c1]

Fosaprepitant dimeglumine is an antiemetic drug, administered intravenously. It is a prodrug of aprepitant. Fosaprepitant dimeglumine is commercially available as a prescription medicine from Merck & Co, under the trade name EMEND® in US and IVEMEND® in Europe.

Fosaprepitant dimeglumine and its process were disclosed in U.S. Pat. No. 5,691,336.

PCT publication no. WO 2010/018595 disclosed a process for the purification of fosaprepitant dimeglumine. According to the publication, fosaprepitant dimeglumine can be prepared by subjecting the solution of dibenzyl {3-[2(R)-[(1R)-1-[3,5-bis(trifluoromethyl)phenyl]ethoxy]-3(S)-(4-fluorophenyl)morpholin-4-yl]-5-oxo-4,5-dihydro-[1,2,4]-triazol-1-yl} phosphonic acid (herein after referred as dibenzyl fosaprepitant) in methanol or tetrahydrofuran to hydrogenation in the presence of palladium carbon and N-methyl-D-glucamine.

PCT publication no. WO 2011/045817 disclosed a process for the preparation of fosaprepitant dimeglumine. According to the publication, fosaprepitant dimeglumine can be prepared by subjecting the solution of dibenzyl fosaprepitant in a solvent such as methanol, ethanol, isopropanol, methyl tert-butyl ether or tetrahydrofuran to hydrogenation in the presence of palladium carbon and N-methyl-D-glucamine.

It has been found that the fosaprepitant dimeglumine produced according to the prior art procedures contains palladium content of above 30 parts per million (ppm). The desired product for reduction of tolerated residual concentration to single digit ppm. There is a need for a reproducible process for the preparation of fosaprepitant dimeglumine.

Thus, an object of the present invention is to provide a novel process for reducing palladium content in fosaprepitant dimeglumine.

SUMMARY OF THE INVENTION

In one aspect, the present invention provides a novel process for reducing palladium content in fosaprepitant dimeglumine, which comprises:
a) providing a solution of fosaprepitant dimeglumine in a solvent;
b) adding SiliaBond® Metal Scavenger to the solution obtained in step (a);
c) maintaining the reaction mass obtained in step (b);
d) adding a solvent to the reaction mass;
e) isolating the wet solid;
f) slurring the wet solid obtained in step (e) with an ester solvent; and isolating fosaprepitant dimeglumine.

In another aspect, the present invention provides a novel process for reducing palladium content in fosaprepitant dimeglumine, which comprises:
a) providing a solution of dibenzyl fosaprepitant in a solvent;
b) subjecting the solution to hydrogenation in the presence of palladium carbon and N-methyl-D-glucamine;
c) adding SiliaBond® Metal Scavenger to the reaction mass obtained in step (b);
d) maintaining the reaction mass;
e) removing the solvent from the reaction mass to obtain a residual solid;
f) adding nitrile solvent to the residual solid obtained in step (e); and
isolating fosaprepitant dimeglumine.

DETAILED DESCRIPTION OF THE INVENTION

The term "room temperature" refers to temperature at about 25 to 35° C.

According to one aspect of the present invention, there is provided a novel process for reducing palladium content in fosaprepitant dimeglumine, which comprises:
a) providing a solution of fosaprepitant dimeglumine in a solvent;
b) adding SiliaBond® Metal Scavenger to the solution obtained in step (a);
c) maintaining the reaction mass obtained in step (b);
d) adding a solvent to the reaction mass;
e) isolating the wet solid;
f) slurring the wet solid obtained in step (e) with an ester solvent; and isolating fosaprepitant dimeglumine.

The solvent used in step (a) and step (d) may preferably be a solvent or mixture of solvents selected form methanol, ethanol, isopropyl alcohol, tert-butyl alcohol, n-butanol, isobutyl alcohol, tetrahydrofuran, diisopropyl ether, tetrahydropyran, 1,4-dioxane, methyl tert-butyl ether, ethyl tert-butyl ether, diethyl ether, di-tert-butyl ether, diglyme, dimethoxyethane, dimethoxymethane and methoxyethane. More preferably the solvents are methanol, ethanol, isopropyl alcohol and teterahydrofuran.

The term "SiliaBond® Metal Scavenger" is used for removing residual metals from post reactions. The toxic nature of transition metals has led to the reduction of tolerated residual concentration in active pharmaceutical ingredients (APIs) to single digit ppm.

Preferably the SiliaBond® Metal Scavenger used in step (b) may be selected from SiliaBond® amine

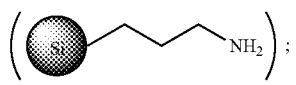

SiliaBond® diamine

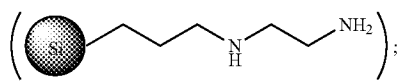

SiliaBond® Triaminetetraacetic Acid

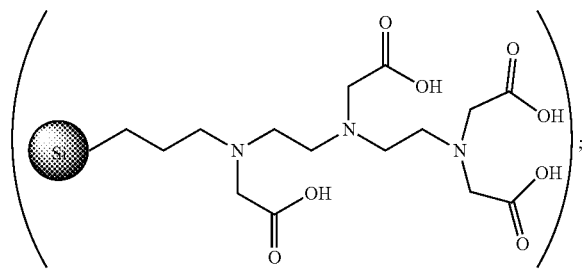

SiliaBond® Thiol

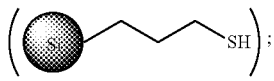

SiliaBond® Thiourea

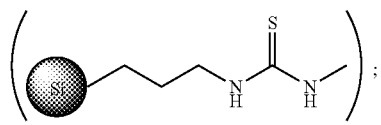

SiliaBond® propyl bromide

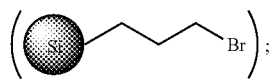

and SiliaBond® dimercaptotriazine

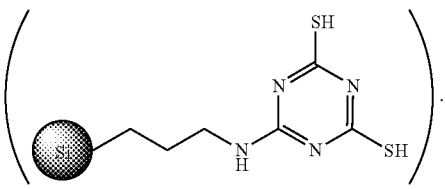

More preferably the SiliaBond® Metal Scavenger is SiliaBond® dimercaptotriazine. SiliaBond® Metal Scavengers are commercially available from SiliCycle® Inc.

The step (c) may conveniently be carried out at room temperature.

Preferably the ester solvent used in step (f) may be a solvent or mixture of solvents selected from ethyl acetate, methyl acetate, isopropyl acetate, tert-butyl methyl acetate and ethyl formate. More preferably the ester solvent is ethyl acetate.

Isolation of fosaprepitant dimeglumine in step (g) may preferably be performed by conventional techniques such as centrifugation and filtration.

According to another aspect of the present invention, there is provided a novel process for reducing palladium content in fosaprepitant dimeglumine, which comprises:
  a) providing a solution of dibenzyl fosaprepitant in a solvent;
  b) subjecting the solution to hydrogenation in the presence of palladium carbon and N-methyl-D-glucamine;
  c) adding SiliaBond® Metal Scavenger to the reaction mass obtained in step (b);
  d) maintaining the reaction mass;
  e) removing the solvent from the reaction mass to obtain a residual solid;
  f) adding nitrile solvent to the residual solid obtained in step (e); and isolating fosaprepitant dimeglumine.

The solvent used in step (a) may preferably be a solvent or mixture of solvents selected form methanol, ethanol, isopropyl alcohol, tert-butyl alcohol, n-butanol, isobutyl alcohol, tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane. More preferably the solvents are methanol, ethanol, isopropyl alcohol and teterahydrofuran.

Preferably the SiliaBond® Metal Scavenger used in step (c) may be selected from SiliaBond® amine, SiliaBond® diamine, SiliaBond® Triaminetetraacetic Acid, SiliaBond® Thiol, SiliaBond® Thiourea, SiliaBond® propyl bromide and SiliaBond® dimercaptotriazine. More preferably the SiliaBond® Metal Scavenger is SiliaBond® dimercaptotriazine.

The step (d) may conveniently be carried out at room temperature.

Removal of the solvent in step (e) may be carried out at atmospheric pressure or at reduced pressure. Removal of the solvent may preferably be carried out until the solvent is almost completely distilled off.

Preferably the nitrile solvent used in step (f) may be a solvent or mixture of solvents selected from acetonitrile, propionitrile, butyronitrile and benzonitrile. More preferably the nitrile solvent is acetonitrile.

Isolation of fosaprepitant dimeglumine in step (g) may preferably be performed by conventional techniques such as centrifugation and filtration.

The invention will now be further described by the following examples, which are illustrative rather than limiting.

PREPARATIVE EXAMPLES

Preparative Example 1

Preparation of dibenzyl fosaprepitant

Aprepitant (50 gm), tetrabenzyl pyrophosphate (75 gm) and teterahydrofuran (635 ml) were added under nitrogen atmosphere at room temperature. The contents were then cooled to 0 to 5° C. and then added sodium hexamethyldisilazane (266.6 ml) slowly for 45 minutes. The reaction mass was stirred for 30 minutes at 0 to 5° C. and then added sodium bicarbonate solution (8%, 1700 ml) and methyl tert-butyl ether (1700 ml) at room temperature. The layers were separated and the organic layer was washed with saturated sodium hydrogen sulfite solution. Again the layers were separated and the organic layer was washed with water. The organic layer was dried with sodium sulfate and the solvent was distilled off under vacuum at 30 to 35° C. to obtain 68 gm of dibenzyl fosaprepitant.

Preparative Example 2

Preparation of fosaprepitant dimeglumine

Dibenzyl fosaprepitant (50 gm) as obtained in preparative example 1, N-methyl-D-glucamine (25 gm), palladium carbon (10 gm) and methanol (410 gm) were added at room temperature and then applied 40 percent hydrogen pressure for 5 hours. The reaction mass was filtered through hyflow-bed and the solvent was distilled off under vacuum pressure at 30 to 35° C. to obtain a residual solid. The residual solid obtained was co-distilled with isopropyl alcohol and acetonitrile. To the reaction mass was added acetonitrile (200 ml) under nitrogen atmosphere and stirred for 15 hours at room temperature. The solid obtained was collected by filtration and dried to obtain 29 gm of fosaprepitant dimeglumine (Palladium content: 30 ppm).

EXAMPLES

Example 1

Fosaprepitant dimeglumine (10 gm; Palladium content: 30 ppm) as obtained in preparative example 2 was dissolved in methanol (100 ml) and stirred for 15 minutes to obtain a solution. To the solution was added SiliaBond® dimercaptotriazine (1 gm) and then maintained for 16 hours at room temperature. The reaction mass was filtered through hyflow-bed and washed with methanol. To the filtrate thus obtained was added isopropyl alcohol (375 ml) slowly for 1 hour. The reaction mass was stirred for 1 hour at 20 to 25° C. and filtered. To the wet solid thus obtained was added ethyl acetate (100 ml) and maintained for 1 hour. The separated solid was filtered and dried to obtain 8 gm of fosaprepitant dimeglumine (Palladium content: 2 ppm).

Example 2

Dibenzyl fosaprepitant (50 gm), N-methyl-D-glucamine (25 gm), palladium carbon (10 gm) and methanol (410 gm) were added at room temperature and then applied 40 percent hydrogen pressure for 5 hours. The reaction mass was filtered through hyflow-bed. To the filtrate thus obtained was added SiliaBond® dimercaptotriazine (5 gm) and maintained for 15 hours at room temperature. The reaction mass was filtered through hyflow-bed and the solvent was distilled off under vacuum pressure at 30 to 35° C. to obtain a residual solid. The residual solid obtained was co-distilled with isopropyl alcohol and acetonitrile. To the reaction mass was added acetonitrile (200 ml) under nitrogen atmosphere and stirred for 15 hours at room temperature. The solid obtained was collected by filtration and dried to obtain 28 gm of fosaprepitant dimeglumine (Palladium content: 3 ppm).

Example 3

A solution of fosaprepitant dimeglumine (30 gm; Palladium content: 3 ppm) as obtained in example 2 in methanol (300 ml) was added to isopropyl alcohol (600 ml) slowly for 45 minutes at room temperature. The reaction mass was stirred for 1 hour at 20 to 25° C. and filtered. The solid thus obtained was added to ethyl acetate (250 ml) and maintained for 1 hour at room temperature. The separated solid was filtered and dried to obtain 24 gm of fosaprepitant dimeglumine (Palladium content: 3 ppm).

We claim:
1. A process for reducing palladium content in fosaprepitant dimeglumine, which comprises:
   a. providing a solution of fosaprepitant dimeglumine in a solvent;
   b. adding a metal scavenger to the solution obtained in step (a);
   c. maintaining the reaction mass obtained in step (b) at room temperature;
   d. adding a solvent to the reaction mass;
   e. isolating the wet solid;
   f. slurring the wet solid obtained in step (e) with an ester solvent; and
   g. isolating fosaprepitant dimeglumine having single digit ppm of residual palladium; wherein the metal scavenger is

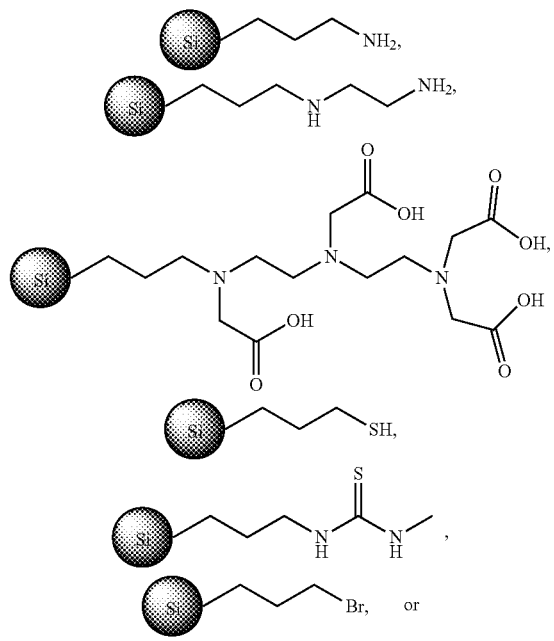

-continued

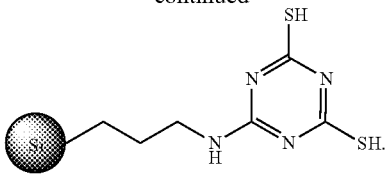

2. The process as claimed in claim 1, wherein the solvent used in step (a) and step (d) is a solvent or mixture of solvents selected form methanol, ethanol, isopropyl alcohol, tert-butyl alcohol, n-butanol, isobutyl alcohol, tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane.

3. The process as claimed in claim 2, wherein the solvents are methanol, ethanol, isopropyl alcohol and teterahydrofuran.

4. The process as claimed in claim 1, wherein the metal scavenger used in step (b) is

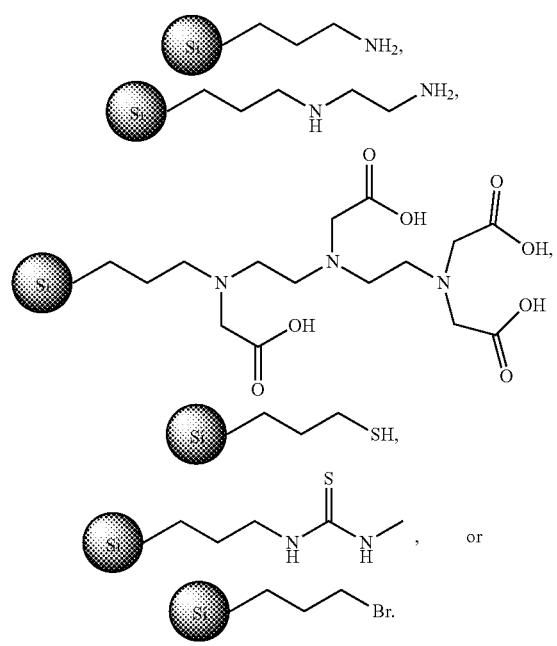

5. The process as claimed in claim 1, wherein the metal scavenger is

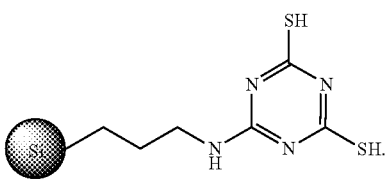

6. The process as claimed in claim 1, wherein the ester solvent used in step (f) is a solvent or mixture of solvents selected from ethyl acetate, methyl acetate, isopropyl acetate, tert-butyl methyl acetate and ethyl formate.

7. The process as claimed in claim 6, wherein the ester solvent is ethyl acetate.

8. A process for reducing palladium content in fosaprepitant dimeglumine, which comprises:
   a. providing a solution of dibenzyl fosaprepitant in a solvent;
   b. subjecting the solution to hydrogenation in the presence of palladium carbon and N-methyl-D-glucamine;
   c. adding a metal scavenger to the reaction mass obtained in step (b);
   d. maintaining the reaction mass at room temperature;
   e. removing the solvent from the reaction mass to obtain a residual solid;
   f. adding nitrile solvent to the residual solid obtained in step (e); and
   g. isolating fosaprepitant dimeglumine having single digit ppm of residual palladium, wherein the metal scavenger is

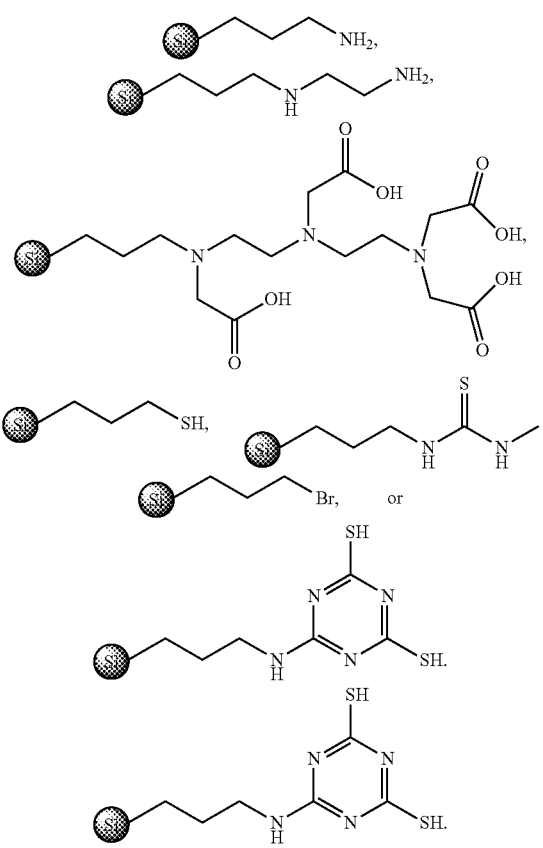

9. The process as claimed in claim 8, wherein the solvent used in step (a) is a solvent or mixture of solvents selected form methanol, ethanol, isopropyl alcohol, tert-butyl alcohol, n-butanol, isobutyl alcohol, tetrahydrofuran, diisopropyl ether, tertrahydropyran, 1,4-dioxane, methyl tert-butyl ether, ethyl tert-butyl ether, diethyl ether, di-tert-butyl ether, diglyme, dimethoxyethane, dimethoxymethane and methoxyethane.

10. The process as claimed in claim 9, wherein the solvents are methanol, ethanol, isopropyl alcohol and teterahydrofuran.

11. The process as claimed in claim 8, wherein the metal scavenger used in step (c) is

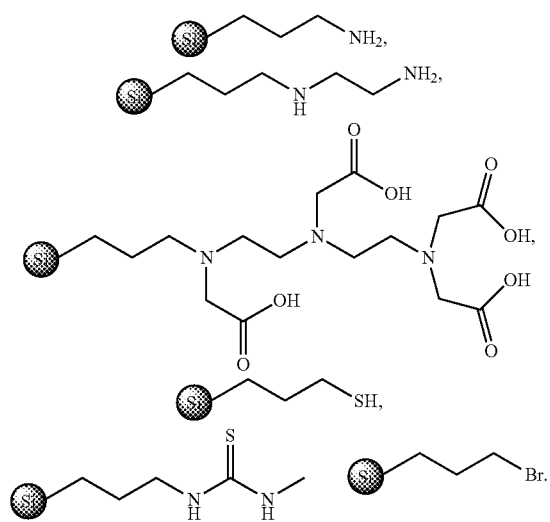
12. The process as claimed in claim 8, wherein the metal scavenger is
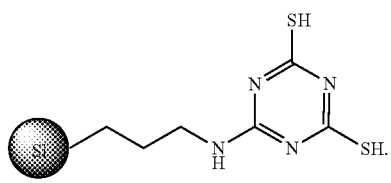
13. The process as claimed in claim 8, wherein the nitrile solvent used in step (f) is a solvent or mixture of solvents selected from acetonitrile, propionitrile, butyronitrile and benzonitrile.
14. The process as claimed in claim 13, wherein the nitrile solvent is acetonitrile.
* * * * *